United States Patent
Cherry

(10) Patent No.: US 10,543,499 B1
(45) Date of Patent: Jan. 28, 2020

(54) DISPOSABLE POWDER-DISPENSING BULB

(71) Applicant: Karriem Cherry, Lynn, MA (US)

(72) Inventor: Karriem Cherry, Lynn, MA (US)

( * ) Notice: Subject to any disclaimer, the term of this patent is extended or adjusted under 35 U.S.C. 154(b) by 0 days.

(21) Appl. No.: 15/919,288

(22) Filed: Mar. 13, 2018

(51) Int. Cl.
| B05B 11/04 | (2006.01) |
|---|---|
| B05B 11/00 | (2006.01) |
| B65D 47/20 | (2006.01) |
| A61J 1/06 | (2006.01) |

(52) U.S. Cl.
CPC ........ B05B 11/048 (2013.01); B05B 11/0059 (2013.01); *A61J 1/067* (2013.01); *A61M 2202/064* (2013.01); *B65D 47/20* (2013.01)

(58) Field of Classification Search
CPC .... B05B 11/048; B05B 11/0059; A61J 1/067; A61M 2202/064; B65D 47/20
USPC ....... 222/206, 207, 211, 213, 215, 478, 481, 222/482
See application file for complete search history.

(56) References Cited

U.S. PATENT DOCUMENTS

| 2,207,834 | A | * | 7/1940 | Stern | B05B 11/041 |
|---|---|---|---|---|---|
| | | | | | 222/215 |
| 2,554,489 | A | | 5/1951 | Crane | |
| 3,411,674 | A | * | 11/1968 | Gould | B65D 35/08 |
| | | | | | 222/215 |
| 4,091,966 | A | | 5/1978 | Laauwe | |
| 4,730,751 | A | | 3/1988 | Mackles | |
| 5,033,655 | A | * | 7/1991 | Brown | B29C 65/568 |
| | | | | | 222/212 |
| 5,215,221 | A | | 6/1993 | Dirksing | |
| 5,894,967 | A | | 4/1999 | Stahley | |
| 6,311,872 | B1 | | 11/2001 | Bongiovanni | |
| D504,979 | S | | 5/2005 | Lai | |
| 8,162,186 | B2 | * | 4/2012 | Maxwell | B65D 1/32 |
| | | | | | 222/212 |
| 2002/0121530 | A1 | * | 9/2002 | Socier | B65D 47/2031 |
| | | | | | 222/494 |
| 2007/0160543 | A1 | * | 7/2007 | Moller | A61J 1/067 |
| | | | | | 424/46 |
| 2007/0164060 | A1 | | 7/2007 | Hayday | |
| 2013/0105599 | A1 | * | 5/2013 | Chen | B05B 11/045 |
| | | | | | 239/329 |
| 2018/0280639 | A1 | * | 10/2018 | Alexander | A61M 15/0086 |

FOREIGN PATENT DOCUMENTS

WO 1998018565 A 5/1998

* cited by examiner

*Primary Examiner* — Donnell A Long

(57) ABSTRACT

The disposable powder-dispensing bulb is configured for use with talcum powder. The disposable powder-dispensing bulb stores the talcum powder. The disposable powder-dispensing bulb dispenses the talcum powder. The disposable powder-dispensing bulb is disposable. The disposable powder-dispensing bulb is degradable after disposal. The disposable powder-dispensing bulb comprises a degradable bulb, a degradable cap, and talcum powder. The degradable bulb is a hollow containment structure. The talcum powder is stored in the degradable bulb. The degradable cap attaches to the degradable bulb. The degradable cap opens and closes to provide access to the talcum powder stored within the degradable bulb.

11 Claims, 3 Drawing Sheets

US 10,543,499 B1

DISPOSABLE POWDER-DISPENSING BULB

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of health including medical and veterinary science, more specifically, a bulb type air pump for dispensing powder onto a body.

SUMMARY OF INVENTION

The disposable powder-dispensing bulb is configured for use with talcum powder. The disposable powder-dispensing bulb stores the talcum powder. The disposable powder-dispensing bulb dispenses the talcum powder. The disposable powder-dispensing bulb is disposable. The disposable powder-dispensing bulb is degradable after disposal. The disposable powder-dispensing bulb comprises a degradable bulb, a degradable cap, and talcum powder. The degradable bulb is a hollow containment structure. The talcum powder is stored in the degradable bulb. The degradable cap attaches to the degradable bulb. The degradable cap opens and closes to provide access to the talcum powder stored within the degradable bulb.

These together with additional objects, features and advantages of the disposable powder-dispensing bulb will be readily apparent to those of ordinary skill in the art upon reading the following detailed description of the presently preferred, but nonetheless illustrative, embodiments when taken in conjunction with the accompanying drawings.

In this respect, before explaining the current embodiments of the disposable powder-dispensing bulb in detail, it is to be understood that the disposable powder-dispensing bulb is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the disposable powder-dispensing bulb.

It is therefore important that the claims be regarded as including such equivalent construction insofar as they do not depart from the spirit and scope of the disposable powder-dispensing bulb. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
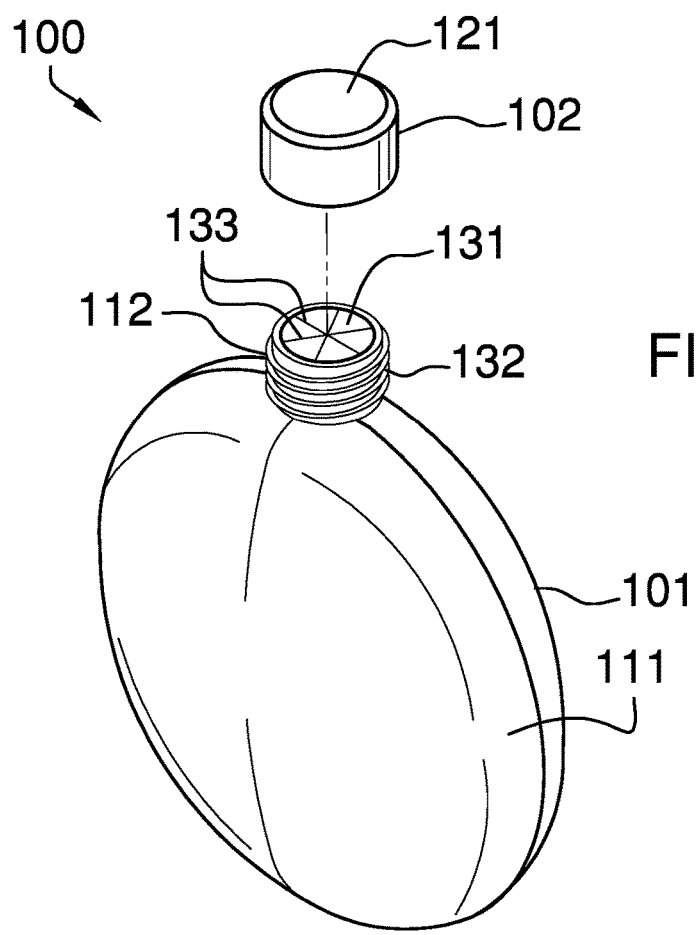
FIG. 1 is a perspective view of an embodiment of the disclosure.
Figure 2:
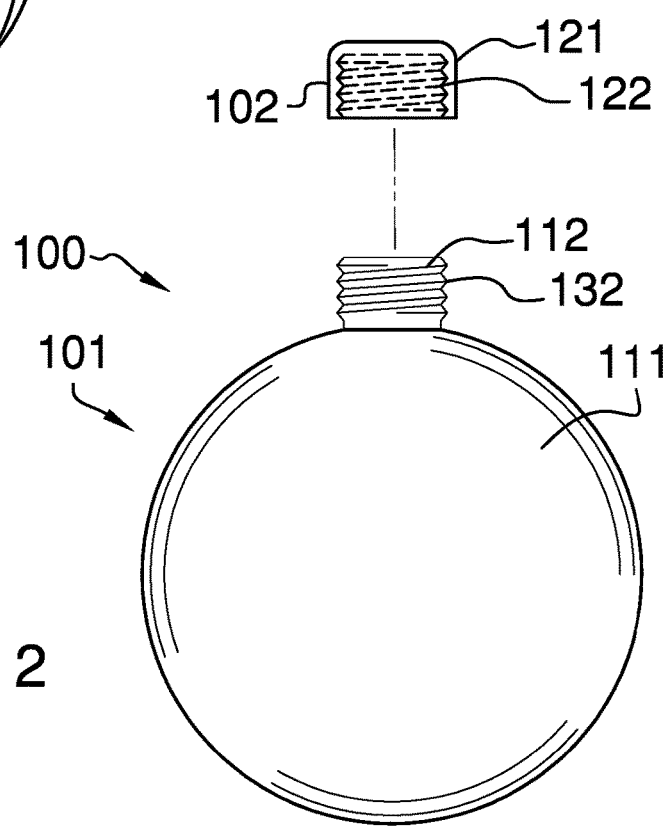
FIG. 2 is a front view of an embodiment of the disclosure.
Figure 3:
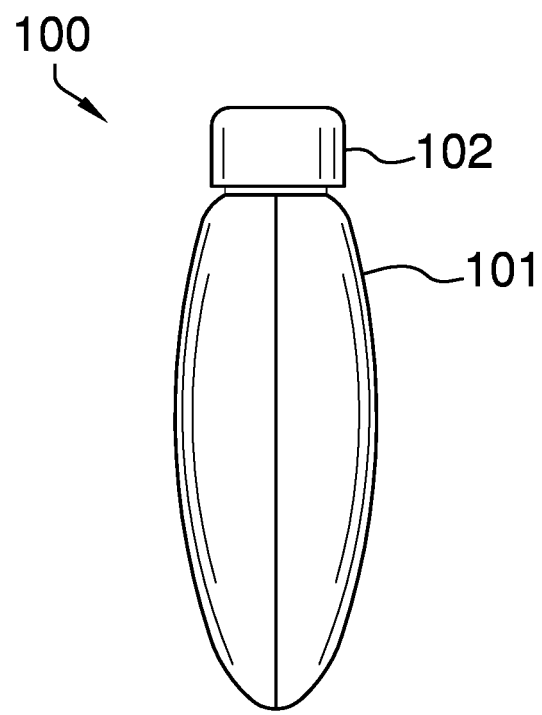
FIG. 3 is a side view of an embodiment of the disclosure.
Figure 4:
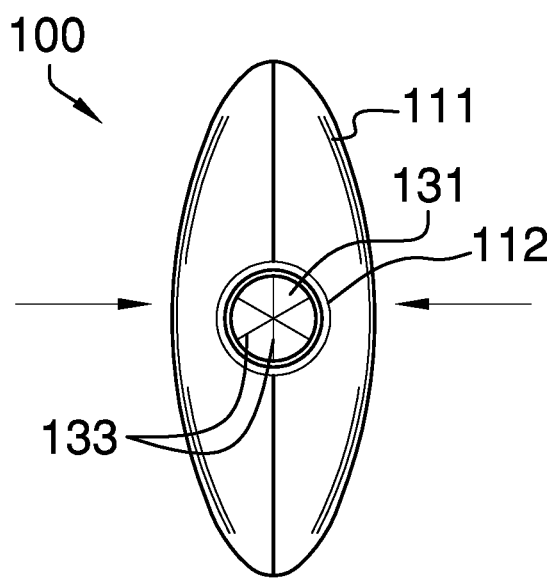
FIG. 4 is a top view of an embodiment of the disclosure.
Figure 5:
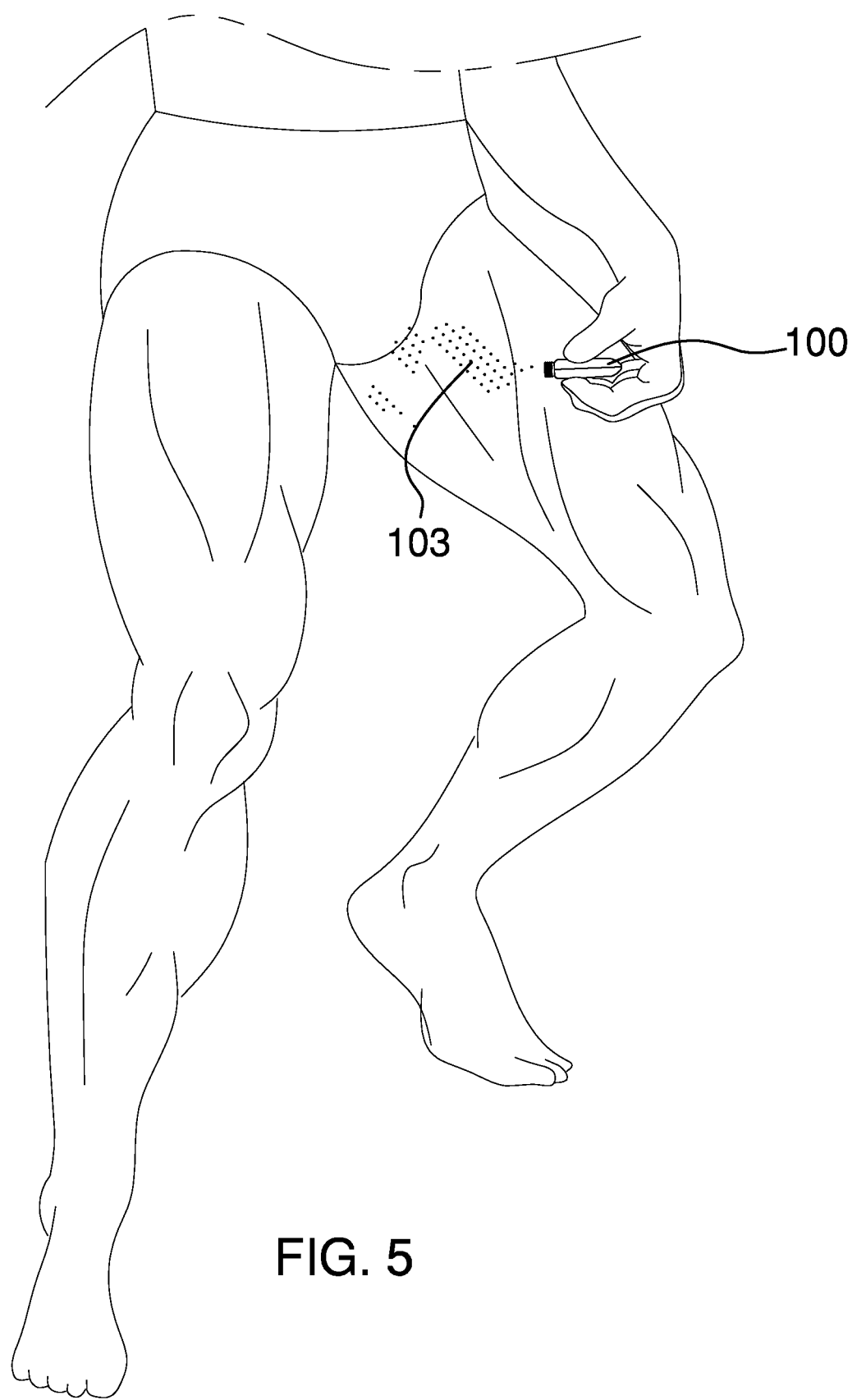
FIG. 5 is an in-use view of an embodiment of the disclosure.

Detailed reference will now be made to one or more potential embodiments of the disclosure, which are illustrated in FIGS. 1 through 5.

The disposable powder-dispensing bulb 100 (hereinafter invention) is configured for use with talcum powder 103. The invention 100 stores the talcum powder 103. The invention 100 dispenses the talcum powder 103. The invention 100 is disposable. The invention 100 is degradable after disposal. The invention 100 comprises a degradable bulb 101, a degradable cap 102, and talcum powder 103. The degradable bulb 101 is a hollow containment structure. The degradable bulb 101 stores the talcum powder 103. The degradable cap 102 attaches to the degradable bulb 101. The degradable cap 102 opens and closes the degradable bulb 101 to provide access to the talcum powder 103 stored within the degradable bulb 101.

The degradable bulb 101 is a hollow containment device. The degradable bulb 101 is a fluid impermeable structure that stores the talcum powder 103. The fluid impermeable structure of the degradable bulb 101 protects the talcum powder 103 from contamination by a liquid. The degradable bulb 101 is a semi-rigid structure with an elastic nature. The degradable bulb 101 is a disposable structure. The degradable bulb 101 is formed from a degradable plastic.

In the first potential embodiment of the disclosure, the degradable bulb 101 is formed from a copolymer comprising polylactic acid (CAS 26100-51-6) and caprolactone polymer (CAS 24980-41-4). The degradable bulb 101 degrades in a manner suitable for use as compost. The polylactic acid (CAS 26100-51-6) degrades into lactic acid. A variety of bacteria and fungi will degrade the caprolactone polymer (CAS 24980-41-4) in both aerobic and anaerobic conditions.

The degradable bulb 101 comprises a bulb body 111 and a spout 112.

The bulb body 111 is a rounded disk-structure. The bulb body 111 is a hollow structure that forms the containment space of the degradable bulb 101. The bulb body 111 is a semi-rigid structure with an elastic nature. As the bulb body 111 is compressed, the volume of the containment space decreases. This decrease in containment space volume forces the atmosphere out of the bulb body 111 taking with it a portion of the talcum powder 103 contained within the bulb body 111. Once the compressive force is removed from the bulb body 111, the bulb body 111 returns to its relaxed shape thereby replacing the atmospheric gases previously ejected.

The spout 112 is a prism-shaped hollow tubular structure. In the first potential embodiment of the disclosure, the spout 112 has a cylindrical structure. The spout 112 forms a channel into the containment space of the bulb body 111. The talcum powder 103 is ejected from the bulb body 111 through the spout 112. The spout 112 comprises a mister 131 and an exterior screw thread 132.

The mister 131 is a mechanical structure that disperses the talcum powder 103 into the atmosphere as the talcum powder 103 is ejected from the bulb body 111. The mister 131 is a circular disk structure that mounts in the end of the spout 112 that is distal from the bulb body 111. The mister 131 further comprises a plurality of radial slits 133. Each of the plurality of radial slits 133 is formed from the center axis of the spout 112 to the interior surface of the spout 112. As the ejected atmosphere is forced through the plurality of radial slits 133 of the mister 131, the particles of the talcum powder 103 are physically separated from each other as they are forced through the plurality of radial slits 133 of the mister 131. This separation of the talcum powder 103 by the mister 131 serves to disperse the talcum powder 103 into the atmosphere.

The exterior screw thread 132 is an exterior screw thread 132 formed on the exterior surface of the spout 112. The exterior screw thread 132 is sized such that the exterior screw thread 132 can be screwed into the interior screw thread 122 of the capped tube 121 to form the threaded connection. The exterior screw thread 132 and threaded connection are defined in greater detail elsewhere in this disclosure.

The degradable cap 102 is a closure that attaches to the degradable bulb 101. The degradable cap 102 is a fluid impermeable structure that encloses the degradable bulb 101 when the talcum powder 103 is not in use. The degradable cap 102 is a disposable structure. The degradable cap 102 is formed from a degradable plastic.

The degradable cap 102 is formed from a copolymer comprising polylactic acid (CAS 26100-51-6) and caprolactone polymer (CAS 24980-41-4). In the first potential embodiment of the disclosure, the degradable cap 102 degrades in a manner suitable for use as compost. The polylactic acid (CAS 26100-51-6) degrades into lactic acid. A variety of bacteria and fungi will degrade the caprolactone polymer (CAS 24980-41-4) in both aerobic and anaerobic conditions.

The degradable cap 102 comprises a capped tube 121 and an interior screw thread 122.

The capped tube 121 is a cylindrical structure that attaches to the spout 112. The capped tube 121 encloses the bulb body 111 by sealing the spout 112. The interior screw thread 122 is an interior screw thread 122 that is formed on the interior surface of the capped tube 121. The interior screw thread 122 forms a threaded connection with the exterior screw thread 132 of the spout 112 to seal the spout 112. The interior screw thread 122 and threaded connection are defined in greater detail elsewhere in this disclosure.

The talcum powder 103 refers to a commercially available powdered substance commonly used for hygiene purposes. The talcum powder 103 is defined in greater detail elsewhere in this disclosure. The degradable bulb 101 stores the talcum powder 103. The talcum powder 103 is removed from the degradable bulb 101 by squeezing the degradable bulb 101.

By squeezing the talcum powder 103, the volume of the containment space within the degradable bulb 101 is reduced. The reduction of volume increases the pressure of the atmosphere within the degradable bulb 101 which ejects a portion of the atmosphere within the degradable bulb 101. The ejection of the atmosphere pulls with it the talcum powder 103 which is then dispersed into the atmosphere and onto a targeted surface.

The following definitions were used in this disclosure:

Atmosphere: As used in this disclosure, the atmosphere refers to a blanket of gases (primarily nitrogen and oxygen) that surround the earth. Typical atmospheric conditions are approximated and characterized by the normal temperature and pressure.

Biodegradable, Degradable, and Photodegradable: As used in this disclosure, a material is degradable if the chemical composition of the material undergoes decomposition under the conditions of normal temperature and pressure. A material is biodegradable if the chemical composition of the material undergoes decomposition by the action of microorganisms. A material is photodegradable if the chemical composition of the material undergoes decomposition when exposed to light. In the vernacular, the use of the term biodegradable often includes degradable and photodegradable materials.

Cap: As used in this disclosure, a cap is a protective cover that encloses a space.

Capped Tube: As used in this disclosure, a capped tube is a tube with one closed end and one open end.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Channel: As used in this disclosure, a channel is a tubular passage through which an object or fluid is passed through.

Closed Position: As used in this disclosure, a closed position refers to a movable barrier structure that is in an orientation that prevents passage through a port or an aperture. The closed position is often referred to as an object being "closed." Always use orientation.

Compress: In this disclosure, compress means to force into a smaller space.

Copolymer: As used in this disclosure, a copolymer is a polymer formed from two or more repeating molecules (also referred to as monomers).

Cylinder: As used in this disclosure, a cylinder is a geometric structure defined by two identical flat and parallel ends, also commonly referred to as bases, which are circular in shape and connected with a single curved surface, referred to in this disclosure as the lateral face. The cross-section of the cylinder remains the same from one end to another. The axis of the cylinder is formed by the straight line that connects the center of each of the two identical flat and parallel ends of the cylinder. Unless otherwise stated within this disclosure, the term cylinder specifically means a right cylinder which is defined as a cylinder wherein the curved surface perpendicularly intersects with the two identical flat and parallel ends.

Decomposition: As used in this disclosure, decomposition refers a chemical process comprising the separation of a molecule of a given atomic mass into two or more molecules or elements, each of lesser atomic mass than the original molecule. Unless stated otherwise in this disclosure, this definition excludes the radioactive processes such as radioactive decay.

Disk: As used in this disclosure, a disk is a prism-shaped object that is flat in appearance.

Disposable: As used in this disclosure, an object is disposable if the object is not considered to be reusable.

Elastic: As used in this disclosure, an elastic is a material or object that deforms when a force is applied to it and that is able to return to its relaxed shape after the force is removed. A material that exhibits these qualities is also referred to as an elastomeric material.

Exterior Screw Thread: An exterior screw thread is a ridge wrapped around the outer surface of a tube in the form of a helical structure that is used to convert rotational movement into linear movement.

Flap: As used in this disclosure, a flap is a piece of material that is hinged or otherwise attached to a surface using one side such that the piece of material is positioned in such a way as to cover a hole in the surface.

Fluid: As used in this disclosure, a fluid refers to a state of matter wherein the matter is capable of flow and takes the shape of a container it is placed within. The term fluid commonly refers to a liquid or a gas.

Interior Screw Thread: An interior screw thread is a groove formed around the inner surface of a tube in the form of a helical structure that is used to convert rotational movement into linear movement.

Monomer: As used in this disclosure, a monomer refers to a molecular structure that bonds to itself in a repeating manner to form a polymer.

Normal Temperature and Pressure: As used in this disclosure, normal temperature and pressure refers to atmospheric conditions corresponding to 20 degrees C. at 100 kPa (approx. 1 atmosphere). Normal temperature and pressure is often abbreviated as NTP. See standard temperature and pressure.

Nozzle: As used in this disclosure, a nozzle is a device that receives fluid under pressure and releases the fluid in a controlled manner into an environment.

Open Position: As used in this disclosure, an open position refers to a movable barrier structure that is in an orientation that allows passage through a port or an aperture. The open position is often referred to as an object being "open."

Orientation: As used in this disclosure, orientation refers to the positioning of a first object relative to: 1) a second object; or, 2) a fixed position, location, or direction.

Palm-Size: As used in this disclosure, palm-size refers to an object that would fit in the palm of a hand. This disclosure assumes that a palm-sized object is less than 100 mm as measured across the largest span of the palm-sized object.

Polymer: As used in this disclosure, a polymer refers to a molecular chain that comprises multiple repeating units known as monomers. The repeating unit may be an atom or a molecular structure.

Powder: As used in this disclosure, a powder refers to a dry accumulation of material in a particulate or granular form. Powders will often display fluidic characteristics such as flow and taking the shape of the container the powder is contained in.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Radial: As used in this disclosure, the term radial refers to a direction that: 1) is perpendicular to an identified central axis; or, 2) projects away from a center point.

Relaxed Shape: As used in this disclosure, a structure is considered to be in its relaxed state when no shear, strain, or torsional forces are being applied to the structure.

Rounded: A used in this disclosure, the term rounded refers to the replacement of an apex, vertex, or edge or brink of a structure with a (generally smooth) curvature wherein the concave portion of the curvature faces the interior or center of the structure.

Screw: As used in this disclosure, to screw is a verb meaning: 1) to fasten or unfasten (unscrew) a threaded connection; or 2) to attach a helical structure to a solid structure.

Semi-Rigid Structure: As used in this disclosure, a semi-rigid structure is a solid structure that is stiff but not wholly inflexible and that will deform under force before breaking. A semi-rigid structure may or may not behave in an elastic fashion in that a semi-rigid structure need not return to a relaxed shape.

Spout: As used in this disclosure, a spout is a prism-shaped tube structure through which a fluid or powder flows into or out of a container.

Spray: As used in this disclosure, a spray is a plurality of liquid drops dispersed in a gas.

Spray Nozzle: A spray nozzle is a device that receives liquid under pressure and disperses that liquid into the atmosphere as a spray.

Squeeze: As used in this disclosure, to squeeze means to compress an object by hand.

Talcum Powder: As used in this disclosure, talcum powder is a domestic article used for cosmetic and hygiene purposes. Talcum powder comprises a highly absorbent material that is applied to the skin to absorb moisture that accumulates against the skin. Many versions of talcum powder exist. A common formulation comprises a mixture of magnesium silicate and cornstarch.

Threaded Connection: As used in this disclosure, a threaded connection is a type of fastener that is used to join a first tube-shaped and a second tube-shaped object together. The first tube-shaped object is fitted with a first fitting selected from an interior screw thread or an exterior screw thread. The second tube-shaped object is fitted with the remaining screw thread. The tube-shaped object fitted with the exterior screw thread is placed into the remaining tube-shaped object such that: 1) the interior screw thread and the exterior screw thread interconnect; and, 2) when the tube-shaped object fitted with the exterior screw thread is rotated the rotational motion is converted into linear motion that moves the tube-shaped object fitted with the exterior screw thread either into or out of the remaining tube-shaped object. The direction of linear motion is determined by the direction of rotation.

Tube: As used in this disclosure, a tube is a hollow prism-shaped device formed with two open ends. The tube is used for transporting liquids and gases. The line that connects the center of the first congruent face of the prism to the center of the second congruent face of the prism is referred to as the center axis of the tube or the centerline of the tube. When two tubes share the same centerline they are said to be aligned. When the centerlines of two tubes are perpendicular to each other, the tubes are said to be perpendicular to each other. In this disclosure, the terms inner dimensions of a tube and outer dimensions of a tube are used as they would be used by those skilled in the plumbing arts.

Vernacular: As used in this disclosure, the vernacular is a noun that refers to the common meaning and usage of a word as opposed to a specialized or more specific meaning and usage of the same word by a person skilled in an art.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A dispensing device comprising
a degradable bulb, a degradable cap, and talcum powder;
wherein the degradable cap attaches to the degradable bulb;
wherein the dispensing device stores the talcum powder;
wherein the dispensing device dispenses the talcum powder;
wherein the dispensing device is disposable;
wherein the dispensing device is degradable;
wherein the degradable bulb comprises a bulb body and a spout;
wherein the spout attaches to the bulb body;
wherein the bulb body is a hollow, rounded disk-structure that forms the containment space of the degradable bulb;
wherein the talcum powder is stored in the containment space;
wherein the spout has a cylindrical structure;
wherein the spout further comprises a mister and an exterior screw thread;
wherein the exterior screw thread is formed on the exterior surface of the cylindrical structure;
wherein the mister is a mechanical structure
wherein the mister disperses the talcum powder into the atmosphere;
wherein the mister is a circular disk structure;
wherein the mister mounts in the end of the spout that is distal from the bulb body;
wherein the mister further comprises a plurality of radial slits;
wherein each of the plurality of radial slits is formed from the center axis of the spout to the interior surface of the spout;
wherein the degradable bulb is a hollow containment structure;
wherein the degradable bulb is a fluid impermeable structure;
wherein the degradable bulb stores the talcum powder;
wherein the degradable bulb is a semi-rigid structure with an elastic nature;
wherein the degradable bulb is a disposable structure;
wherein the degradable bulb is formed from a degradable plastic;
wherein the degradable cap opens and closes the degradable bulb;
wherein the degradable cap is a fluid impermeable structure;
wherein the degradable bulb is a semi-rigid structure;
wherein the degradable bulb is a disposable structure;
wherein the degradable bulb is formed from a degradable plastic;
wherein the spout forms a channel into the containment space of the bulb body;
wherein the talcum powder is ejected from the bulb body through the spout.

2. The dispensing device according to claim 1
wherein as the bulb body is compressed the volume of the containment space decreases;
wherein the decrease in containment space volume ejects the atmosphere out of the bulb body;
wherein the ejected atmosphere takes with it a portion of the talcum powder contained within the bulb body;
wherein the ejected atmosphere reenters the bulb body as the bulb body returns to its relaxed shape.

3. The dispensing device according to claim 2 wherein the spout is a prism-shaped hollow tubular structure.

4. The dispensing device according to claim 3 wherein the ejected atmosphere is forced through the plurality of radial slits of the mister.

5. The dispensing device according to claim 4 wherein the talcum powder is physically separated as the talcum powder is forced through the plurality of radial slits of the mister.

6. The dispensing device according to claim 5
wherein the exterior screw thread is an exterior screw thread;
wherein the exterior screw thread is formed on the lateral face of the spout.

7. The dispensing device according to claim 6
wherein the degradable cap comprises a capped tube and an interior screw thread;
wherein the interior screw thread is formed on the interior surface of the capped tube;
wherein the capped tube attaches to the spout.

8. The dispensing device according to claim 7
wherein the capped tube is a cylindrical structure;
wherein the capped tube seals the spout.

9. The dispensing device according to claim 8
wherein the interior screw thread forms a threaded connection with the exterior screw thread;
wherein the exterior screw thread is sized such that the exterior screw thread can be screwed into the interior screw thread of the capped tube to form the threaded connection.

10. The dispensing device according to claim 9
wherein the degradable bulb is formed from a copolymer comprising polylactic acid (CAS 26100-51-6) and caprolactone polymer (CAS 24980-41-4);
wherein the polylactic acid (CAS 26100-51-6) degrades into lactic acid;
wherein bacteria and fungi will degrade the caprolactone polymer (CAS 24980-41-4) in aerobic conditions;
wherein bacteria and fungi will degrade the caprolactone polymer (CAS 24980-41-4) in anaerobic conditions.

11. The dispensing device according to claim 10
wherein the degradable cap is formed from a copolymer comprising polylactic acid (CAS 26100-51-6) and caprolactone polymer (CAS 24980-41-4);
wherein the polylactic acid (CAS 26100-51-6) degrades into lactic acid;
wherein bacteria and fungi will degrade the caprolactone polymer (CAS 24980-41-4) in aerobic conditions;
wherein bacteria and fungi will degrade the caprolactone polymer (CAS 24980-41-4) in anaerobic conditions.

* * * * *